United States Patent [19]

Hansson

[11] 4,225,614

[45] Sep. 30, 1980

[54] METHOD OF TREATMENT FOR MUCOCUTANEOUS HERPES SIMPLEX INFECTIONS

[75] Inventor: Anders E. Hansson, Staffanstorp, Sweden

[73] Assignee: Aktiebolaget Draco, Lund, Sweden

[21] Appl. No.: 969,366

[22] Filed: Dec. 14, 1978

[30] Foreign Application Priority Data

Dec. 21, 1977 [SE] Sweden .................................. 7714578

[51] Int. Cl.$^2$ ..................... A61K 31/315; A61K 33/30
[52] U.S. Cl. ..................................... 424/289; 424/145
[58] Field of Search ................................ 424/145, 289

[56] References Cited

PUBLICATIONS

Shlomai et al., Carcinogensis Abstracts, vol. 13, No. 6, 1975, p. 572.
PDR, 27th Edition, 1973, pp. 541 & 542.

*Primary Examiner*—Jerome D. Goldberg
*Attorney, Agent, or Firm*—Brumbaugh, Graves, Donohue & Raymond

[57] ABSTRACT

A method for treating mucocutaneous herpes simplex infections in man or other animals susceptible to said infections comprising the administration of an amount of zinc in the form of a salt or a hydroxycarboxylic acid or aminocarboxylic acid complex thereof, therapeutically effective in the treatment of said infections.

2 Claims, No Drawings

METHOD OF TREATMENT FOR MUCOCUTANEOUS HERPES SIMPLEX INFECTIONS

The present invention relates to a method for treating mucocutaneous herpes simplex infections in man or other animals susceptible to said infection. More specifically the invention concerns the use of zinc in the form of a salt or hydroxycarboxylic acid or aminocarboxylic acid complex therefor, the amount of said zinc salt or zinc complex administered being therapeutically effective for the treatment of said infections.

The object of the present invention is to treat herpes simplex infections prophylactically or by reducing symptoms manifested at either early or at late stages of said infections.

Recurrent herpes simplex infections are a frustrating problem for both the patient and the physician. Lesions cause discomfort, embarrassment and disrupt normal life patterns. Although many therapeutic modalities have been advocated throughout the years, physicians are still in search of a truly effective treatment for recurrent herpes simplex.

For many years, smallpox vaccinations were used as a treatment for recurrent herpes simplex. This approach to the treatment of herpes simplex had its origins in the Gildermeister and Hertzberg discovery in 1925 Dtsch. Med. Wochenschr. 51, 1647, (1925), that inoculation of herpes simplex virus into rabbit corneas protected against subsequent inoculations of vaccinia virus. From this finding Gildermeister et al. suggested that the herpes simplex and vaccinia viruses were antigenically similar.

In 1963-64, three double-blind studies using idoxuridine (2-deoxy-5-iodouridine) in ointment or cream revealed it to be no more effective than the placebo ointment or cream bases against herpes simplex. Subsequently, Corbett et al., JAMA, 196, 155 (1966), demonstrated in a double-blind study that idoxuridine (0.1 percent) in polyvinyl alcohol significantly shortened the healing time of recurrent herpes simplex lesions when the medication was applied at an early stage of infection.

Felber et al., in 1973, reported JAMA, 223, 289 (1973) on the successful treatment of recurrent herpes simplex with photodynamic inactivation with neutral red dye and fluorescent light. Herpes simplex virus can be inactivated in vitro if exposed to any of several petrotricyclic dyes and ordinary fluorescent light.

A recently proposed therapeutical approach to herpes simplex virus involved the use of topical solvents, such as chloroform or ether. Since the envelope around the herpes simplex virus in ether-labile, it has been postulated that the envelope may be removed or so altered with ether that the virus structure becomes vulnerable to the natural host defense mechanism. Chloroform has an apparent similar effect. In an uncontrolled study, Nugent and Chou reported in JAMA, 224, 132 (1973) on the successful treatment of six patients with ether or chloroform. Sabin also reported in N. Engl. J. Med. 293, 986 (1973) on the successful results with ether in an uncontrolled series.

Philpott, in United States Pharmacopeia, XIX, p 104-105, July 1, 1975, has stated that flexible collodion USP, which contains 71 percent ether, seems to be an effective and practical approach to herpes simplex virus therapy in his practice.

Bacillus Calmette-Guerin (BCG) may be a nonspecific stimulant of cell-mediated immunity in the prevention of recurrent herpes simplex. In an uncontrolled study, Anderson et al. reported, in Obstet. Gynecol. 43, 797, (1974) on a dramatic decrease in frequency of infections in fifteen female patients with recurrent herpes progenitalis treated with BCG immunization. Although they reported no complications in their patients, it should be mentioned that BCG immunization for the therapy of recurrent herpes has several real and theoretical disadvantages. The most obvious disadvantage is that BCG immunization converts PPD skin tests, thus eliminating a valuable test for the early diagnosis of tuberculosis. Other disadvantages are hypersensitivity syndromes. Specific complications include keloid formation, severe or protracted ulceration, lymphadenopathy, and lupus vulgaris.

Levamisole is a broad-spectrum anthelmintic drug which is presently under investigation in the United States. It appears to enhance host defense mechanisms such as macrophage function and to stimulate host immunologic mechanisms. In N. Engl. J. Med. 29, 308, (1975) Kent reported positive results in twelve of fifteen patients with recurrent herpes labialis in an uncontrolled study involving the use of Levamisole.

Y. J. Gordon et al., *Antimic. Agents Chemother.* 8, 377 (1975) have reported that zinc ions irreversibly inhibit replication of herpes simplex virus in BSC-1 [define] cells, whereby a concentration of 0.1 mM inhibited the synthesis of infectious virus progency by 95 to 96%. There is however no teaching of the treatment of herpes simplex virus infections in vivo.

Surprisingly, it has now been shown that it is possible to treat herpes simplex virus infections and to reduce symptoms thereof by means of a preparation according to the present invention. Said preparation is essentially characterized in that it contains a therapeutically effective amount of zinc in the form of a salt or complex thereof, together with inert filling agents and carriers known per se, and in the form of peroral dosage units.

Zinc is preferably administered as a complex of a hydroxycarboxylic acid, or an aminocarboxylic acid in an aqueous solution, the pH of which is from about 3 to 9 and preferably 3 to 6. The hydroxycarboxylic acid is selected from the group consisting of α-hydroxycarboxylic acids such as citric acid, tartaric acid, malic acid, lactic acid and glycolic acid. The aminocarboxylic acid is selected from the group consisting of the group α-aminocarboxylic acids such as amino-acetic acid, aspartic acid, aspargine, glutamic acid, glutamine and ethylenediamine tetracetic acid. An equimolecular relation exists between the complex former, and zinc. Accordingly, the preferred preparation exists as a dosage unit in dry form, which prior to administration is dissolved in water.

Zinc may also be administered in the form of a thereapeutically acceptable salt. Suitable salts include zinc chloride, zinc nitrate, zinc sulphate, zinc carbonate, and zinc acetate. In accordance with the present invention said zinc salts may be administered in the form of peroral dosage units such as tablets, powder and solutions.

In preparing a composition of the present invention in the form of dosage units for oral administration, the active zinc compound selected may be mixed with a solid pulverulent carrier such as lactose, saccharose, sorbitol, mannitol, starch, (e.g. potato starch, corn starch, amylopectin), cellulose derivatives or gelatine, as well as with an antifriction agent such as magnesium stearate, calcium stearate, polyethyleneglycol waxes or the like, and pressed into tablets. If coated tablets are desired, the core of the aforementioned composition may be coated with concentrated solution of sugar, which may contain, e.g., gum arabicum, gelatine, talc, titaniumdioxide or the like. Furthermore, the tablets may be coated with a lacquer dissolved in an easily volatile organic solvent or mixture of solvents.

In the preparation of soft gelatine capsules (pearl-shaped, closed capsules), which consist of gelatine, and e.g. glycerine, or in the preparation of similar closed capsules, the active compound is mixed with a vegetable oil. Hard gelatine capsules may contain granules of the active compound in combination with a solid, pulverulent carrier such as lactose, saccharose, sorbitol, mannito, starch (such as potato starch, corn starch or amylopectin), cellulose derivatives or gelatine.

Liquid preparations for oral administration may be in the form of syrups or suspensions, e.g. solutions containing from about 0.02% by weight to about 20% by weight of the active zinc salt or zinc complex described hereinabove, in combination with sugar and a mixture of ethanol, water, glycerol and propylene glycol. If desired, such liquid preparations may contain coloring agents, flavoring agents, saccharine and carboxymethylcellulose as a thickening agent.

The preparation of pharmaceutical tablets for peroral use is carried out in accordance with the following method:

The solid substances used in the present invention are ground or sieved to a desired particle size. A binding agent is then homogenized and suspended in a suitable solvent. The therapeutic compound and necessary auxiliary agents are mixed under continuous mixing conditions with the binding agent solution, with the mixture being moistened so that the solution is uniformly divided in the mass without overmoistening any part thereof. The amount of solvent is usually so adapted that the mass obtains a consistency similar to wet snow. The moistening of the pulverulent mixture with the binding agent solution causes the particles to slightly form aggregates and the real granulating process is carried out in such a way that the mass is pressed through a sieve in the form of a net of stainless steel having a mesh size of about 1 mm. The resultant mass is then placed in thin layers on a tray to be dried in a drying cabinet. This drying takes place during 10 hours and has to be standarized carefully, since the degree of dampness of the granulate is of utmost importance. Drying in a fluid bed may also be used, and in this case the mass is poured into a container having a net bottom. After the drying stage, the granules are sieved so that the desired particle size is obtained. Under certain circumstances powder has to be removed.

In the final composition mixture, disintegrating, lubricating and antiadhesive agents are added. After this mixture is formed, the mass has the proper composition for tabletting.

A cleaned tablet punch machine is provided with a set of punches and dies. Suitable adjustments for the weight of the tablets and the degree of compression are predetermined. The weight of the tablets is decisive for the size of the dose in each tablet and is calculated starting from the amount of therapeutic agent in the granules. The degree of compression affects the size of the tablet, its strength and its ability to disintegrate in water. As regards the two later properties the choice of compression pressure (0.5 to 5 ton) means something of a balancestep [explain]. When the proper adjustment of the punching machine is set, the formation of tablets is commenced and carried out at a rate of 20,000 to 200,000 tablets per hour. The pressing of the tablets requires different times and depends on the size of the batch.

The tablets are freed from adhering powder in a specific apparatus and are then stored in closed packages until they are delivered.

Many tablets, especially those which are rough or bitter, are coated with a layer of sugar or some other suitable coating.

The tablets are usually packed by machines having an electronic counting device. The different types of packages consist of a glass or plastic gallipots, but also boxes, tubes and specific dosage adapted packages.

The daily dose of the active substance varies and depends on the type of administration, but as a general rule it is 10 to 500 mg/per day of zinc for peroral administration.

The present invention is further described in detail in accordance with the following Examples:

EXAMPLE 1

Zinc sulphate, pulverulent: 0.100 kg
Sorbitol: 0.400 kg
Sodium Bicarbonate: 0.300 kg
Citric acid: 0.400 kg
Flavoring agents: q.s.

After drying, the ingredients were mixed and the mass was tabletted in a tabletting machine for effervescent tablets. It was determined that each tablet contained 40 mg of zinc and when dissolved in 100 ml of water prior to peroral administration that the pH was 4.3.

EXAMPLE 2

Zinc sulphate, pulverulent: 0.125 kg
Sugar: 4.000 kg
Tartaric acid: 0.700 kg
Sodium bicarbonate: 0.600 kg
Flavoring agents: q.s.

The pulverulent ingredients were dried and well mixed and packed in airtight bags. Each dose corresponded to 45 mg of zinc and was intended to be dissolved in 100 ml of water prior to administration (p.o).

EXAMPLE 3

Zinc chloride: 0.094 kg
Sugar: 0.400 kg
Citric acid: 0.400 kg
Sodium hydroxide to pH 4.5: q.s.
Flavoring agents: q.s
Water: 100 l Zinc chloride, sugar, citric acid, and flavoring agents were dissolved in the major portion of the water. The pH was adjusted to 4.5 using sodium hydroxide. The remaining amount of water was added to final volume, whereupon the solution was dispensed. 100 ml of solution corresponds to 45 mg of zinc.

EXAMPLE 4

Zinc carbonate: 0.100 kg
Microcrystalline cellulose: 0.100 kg
Lactose: 0.100 kg

Magnesium stearate: 0.002 kg
Flavoring agents: q.s

The pulverulent substances were sieved and mixed. The mass was compacted in a tabletting machine, ground through a 1 mm sieve and mixed again. Thereafter the composition was tabletted in a tabletting machine with tablet weight 0.3 g.

The herpes simplex infections can be treated prophylactically and/or therapeutically.

It is thus known that the herpes simplex viruses are present in ganglions of the nerve cells and can be activated by changes of climate or environment, as e.g. exposition for bright sunshine. When patients suffering from herpes simplex infections know about a change in climate, as e.g. before a trip to sunny resort places, zinc is administered prophylactically. Thus a treatment using a composition according to Example 1 above is used, whereby the patient is administered 1-3 tablets containing 45 mg $Zn^{2+}$ daily.

In at least 4 patients suffering from herpes simplex infections such prophylactic treatment has been successful during the last 2 years, whereby none of the patients have obtained an outbreak of herpes simplex infection at such a change in climate after prophylactic treatment, and whereby each of said patients have obtained such outbreaks of herpes simplex infections in each case when exposing them to such a change and when not carrying out a prophylactic treatment.

In certain cases herpes simplex infections occur, whereby they are felt by the patients as a pain or tenderness under the skin or in the capillary matrix. When such outbreak of the infection is felt zinc is administered 3 times daily with 45 mg $Zn^{2+}$ each time, whereby the symptoms are eliminated within some days.

The normal healing period of a herpes simplex infection when it has broken out as a wound is about 2 weeks when no previously adapted therapy is used. When zinc is used in such cases the healing period is reduced to between 2 and 7 days. The daily dose then being $3 \times 45$ mg of $Zn^{2+}$.

The inventor himself suffering from mucocutaneous herpes simplex infections has not had any outbreak of the infection during 3 years except for one case, when no prophylactic treatment was used and the outbreak came very rapidly, whereby, however, the wound healed completely after 3 days of treatment using 3 times 45 mg of $Zn^{2+}$ daily.

I claim:

1. A method for treating mucocutaneous herpes simplex infections in man or other animals in need of said treatment, wherein a therapeutically effective amount of zinc is orally administered as an aqueous solution of a complex consisting of a compound selected from the group consisting of α-hydroxycarboxylic and α-aminocarboxylic acids (complex former) and zinc, and wherein the α-hydroxycarboxylic acids are selected from the group consisting of citric, tartaric, malic, lactic and glycolic acids and the α-aminocarboxylic acids are selected from the group consisting of amino acetic acid, aspartic acid, aspargine, glutamic acid glutamine and ethylene diamine tetraacetic acid, the relation between the zinc and said complex former being equimolecular and wherein the pH of said solution is between about 3 to 9.

2. The method according to claim 1, characterized in that the amount of the zinc administered per day ranges between about 10 to 500 mg.

* * * * *